United States Patent [19]

Cooper et al.

[11] Patent Number: 4,552,872

[45] Date of Patent: Nov. 12, 1985

[54] PENETRATING TOPICAL PHARMACEUTICAL COMPOSITIONS CONTAINING CORTICOSTEROIDS

[75] Inventors: Eugene R. Cooper; Maurice E. Loomans, both of Cincinnati; Mahdi B. Fawzi, Fairfield, all of Ohio

[73] Assignee: The Procter & Gamble Company, Cincinnati, Ohio

[21] Appl. No.: 576,065

[22] Filed: Feb. 1, 1984

Related U.S. Application Data

[63] Continuation-in-part of Ser. No. 506,274, Jun. 21, 1983, abandoned.

[51] Int. Cl.$^4$ ................... A61K 31/58; A61K 31/56
[52] U.S. Cl. ................................ 514/175; 514/180
[58] Field of Search ............... 424/238, 243; 514/174, 514/189

[56] References Cited

U.S. PATENT DOCUMENTS

| | | | |
|---|---|---|---|
| 1,974 | 1/1879 | Wickett et al. | 424/243 |
| 296,706 | 8/1881 | Cooper | 424/240 |
| 383,391 | 6/1882 | Cooper | 424/240 |
| 506,273 | 6/1983 | Cooper | 424/54 |
| 506,275 | 6/1883 | Cooper | 424/234 |
| 2,990,331 | 6/1961 | Neumann et al. | 167/65 |
| 3,535,422 | 10/1970 | Cox et al. | 424/164 |
| 3,934,013 | 1/1976 | Poulsen | 424/240 |
| 4,006,218 | 2/1977 | Sipos | 424/54 |
| 4,070,462 | 2/1978 | Ecker | 424/243 |
| 4,075,353 | 2/1978 | Mandy | 424/338 |
| 4,126,681 | 11/1978 | Reller | 424/234 |
| 4,289,764 | 9/1981 | Yarrow | 424/243 |
| 4,299,826 | 11/1981 | Luedders | 424/181 |
| 4,343,798 | 8/1982 | Fawzi | 424/240 |
| 4,444,762 | 4/1984 | Rajadhyaksha | 424/238 |

FOREIGN PATENT DOCUMENTS

| | | | |
|---|---|---|---|
| 1072009 | 2/1980 | Canada | 424/240 |
| 2514873 | 10/1976 | Fed. Rep. of Germany | 424/240 |
| 1133800 | 11/1968 | United Kingdom | 424/240 |

OTHER PUBLICATIONS

"Steroids", by Fieser et al, (1959), Reinhold Publishing Corp., pp. 610–611.
B. Idson, *Cosmetics & Toiletries*, 95, 59, (1980).
M. M. Rieger, *Cosmetics & Toiletries*, 94, 32–37, (1979), and 95, 26–38, (1980).
CA 79: 122,308.
Schaaf and Gross, *Dermatologica*, 106, 357, (1953).
J. Zatz et al., *J. Pharm. Sci.*, 67, 789, (1978).
S. K. Chandrasekaran et al., *J. Pharm. Sci.*, 67, 1370, (1978).
CA 92:153,181j.
H. Barnes et al., *Br. J. Derm.*, 93, 459, (1975).
P. J. W. Ayres et al., *Br. J. Derm.*, 99, 307, (1978).
Rosuold, J. et al., "Effect of Formulation on In Vitro Release and In Vivo Absorption of Corticosteroids from Ointments", *Medd. Novsk Favm Selsk*, 44, 21–45, (1980).
Anjo, D. M. et al., "Methods for Predicting Percutaneous Penetration in Man", *Percutaneous Absorption of Steroids*, pp. 31–51, Academic Press, New York, NY, (1980).

*Primary Examiner*—Elbert L. Roberts
*Attorney, Agent, or Firm*—George W. Allen; Jack D. Schaeffer; Steven J. Goldstein

[57] ABSTRACT

Topical pharmaceutical compositions containing a corticosteroid component and a penetration-enhancing vehicle are disclosed. The vehicle comprises a binary combination of a $C_3$–$C_4$ diol and a "cell-envelope disordering compound". The vehicle provides marked transepidermal and percutaneous delivery of corticosteroids. A method of treating certain rheumatic and inflammatory conditions, systemically or locally, is also disclosed.

34 Claims, No Drawings

PENETRATING TOPICAL PHARMACEUTICAL COMPOSITIONS CONTAINING CORTICOSTEROIDS

CROSS-REFERENCE TO RELATED APPLICATION

This application is a continuation-in-part of the application of Eugene R. Cooper, Maurice E. Loomans and Mahdi B. Fawzi having Ser. No. 506,274 which was filed June 21, 1983 and which is now abandoned.

TECHNICAL FIELD

The present invention relates to topical compositions effective in delivering high levels of certain pharmaceutically-active corticosteroid agents through the integument.

BACKGROUND OF THE INVENTION

Because of the ease of access, dynamics of application, large surface area, vast exposure to the circulatory and lymphatic networks, and non-invasive nature of the treatment, the delivery of pharmaceutically-active agents through the skin has long been a promising concept. This is true whether the bioavailability desired is systemic or dermal, regional or local.

The advantages of this form of delivery include, but are not limited to: avoidance of the risks associated with parenteral treatment; elimination of the inconveniences of parenteral treatment; avoidance of the variable rates of absorption and metabolism inherent in oral treatment; increasing the continuity of drug administration by permitting delivery of agents with short biological half-lives; and elimination of gastrointestinal irritation resulting from exposing the gastrointestinal tract to pharmaceutical actives, preservatives, tableting agents, and the like. Most importantly, topical delivery possesses the potential for effectively treating conditions which are local in nature (or which exhibit local manifestations), systemically as well as locally with the same treatment regimen. Thus, effective compositions to deliver pharmaceutical agents are highly sought after.

However, because it must serve as a barrier to the ingress of pathogens and toxic materials, and the egress of physiologic fluids, the skin is highly impermeable. It must be impermeable to preserve its own integrity while at the same time maintaining the delicate dynamic electrolyte balance of the body. The skin must serve a containment function; it must also function as a microbial, chemical, radiation and thermal barrier.

A good deal of this impermeability of the skin results from the nature of one very thin layer created by normal developmental and physiological changes in the skin. After cells are formed in the basal layer, they begin to migrate toward the skin surface, until they are eventually sloughed off. As they undergo this migration, they become progressively more dehydrated and keratinized. When they reach the surface, just prior to being discarded, they form a thin layer of dense, metabolically inactive cells approximately ten microns (10-15 cells) thick. This layer is called the stratum corneum or the "cornfield layer". As a result of the high degree of keratinization of the cells which comprise the stratum corneum, a formidable barrier is created. Therefore, penetration via the nonpolar route, i.e., across the membrane of these cells, remains most difficult.

Other possible penetration routes are available. First, any mechanism which allows the egress of materials, e.g. the sebaceous apparatus, can be manipulated to allow the ingress of materials. Second, the stratum corneum, though keratinized to a great degree, is composed of about 15% lipid-based intercellular material. This may offer a less formidable route despite the close packing of the cells.

It is known that certain binary skin penetration systems can increase the disorder of these lipids. By so increasing the disorder of the lipid portion of the cell-envelope in the stratum corneum, the lipid packing of the cells can be disrupted. This disruption allows certain pharmaceutically active agents to pass through the stratum corneum. This discovery has been confirmed by differential scanning calorimetery, indicating that certain binary skin penetration enhancement systems eliminate the Tm-2 peak associated with melting of cell-envelope lipids.

Adrenal corticosteroids, and the synthetic analogues thereof, are some of the most useful pharmaceutical actives known in the art. These compounds have the capacity to prevent the development of, or suppress existing, localized heat, redness, tenderness and swelling which characterizes any inflammation of skin or mucous membrane. The utility of these compounds is magnified in a clinical setting by the fact that corticosteroids inhibit this inflammatory response whether the inciting cause or agent is radiant, mechanical, chemical, infectious or immunological. Since the first recognition of the potent anti-inflammatory properties of these compounds in 1949, their therapeutic uses have increased dramatically. The unique biochemical, pharmacologic and physiologic properties of corticosteroids make them almost universally useful in the topical treatment of inflammatory conditions.

Corticosteroids are also useful in treating many conditions when used by systemic application. For example, their potent anti-inflammatory and immunosuppressive effects make them useful in the treatment of most rheumatic conditions and diseases.

While corticosteroids are highly effective in the treatment of the above systemic and local conditions, they suffer from one significant disadvantage. The size and shape of corticosteroids makes them exceedingly difficult to deliver percutaneously. Conventional and commercial topical steroid preparations are only marginally effective in delivering sufficient steroid for immediate treatment of local conditions; systemic steroid treatment by percutaneous delivery from known vehicles is virtually impossible. Accordingly, a vehicle system which increases both the level and speed of penetration of the steroid through the skin would be more efficient in the treatment of localized conditions and, more importantly, would greatly increase the chances of making systemic treatment by topical application viable. Effective systemic delivery of steroids by the topical mode of treatment is highly desirable since the topical treatment would result in a lower level of side effects than those associated with conventional (oral or parenteral) methods of administration when systemic steroid therapies are indicated.

It has now been discovered that steroids can be effectively delivered percutaneously by incorporating them into a specific vehicle which provides an exceptional increase in penetration over conventional steroid vehicles, and, more surprisingly, at a rate which now makes the systemic method of administering steroids percutaneously a practical alternative. Specifically, it has been discovered that a select number of combinations of a binary penetration system comprising a cell-envelope disordering compound and a diol compound, heretofore thought only to be useful in delivering nonsteroidal varieties of anti-inflammatory actives and select substituted adenosine- and guanine-derived antivirals, can consistently and dramatically improve the topical delivery of certain corticosteroids, such as triamcinolone acetonide, when used in a vehicle or formulation which is free of certain common solvents, cosolvents, excipients and lipids other than the selected cell-envelope disordering compound.

U.S. Pat. No. 4,343,798, Fawzi, issued Aug. 10, 1982, describes topical antimicrobial/anti-inflammatory compositions containing $C_5$–$C_{12}$ fatty acids in combination with corticosteroids.

U.S. Pat. No. 3,934,013, Poulsen, issued Jan. 20, 1976, describes topical pharmaceutical compositions containing at least two corticosteroids, propylene glycol, a fatty alcohol and water. The patentee describes the "fatty alcohol ingredient" as any fatty alcohol having from 16–24 carbon atoms and, preferably, as a saturated, monohydric primary alcohol such as cetyl alcohol, stearyl alcohol or behenal alcohol.

U.S. Pat. No. 4,289,764, Yarrow, et al., issued Sept. 15, 1981, describes topical pharmaceutical compositions with increased shelf stability. These compositions comprise a steroid, 15–50% by weight propylene glycol and are buffered to a pH of 2.7–3.3. The specification describes the desirability of thickening the propylene glycol (due to its low viscosity) with a compound selected from long-chain paraffins, fatty alcohols, and waxes, including cetyl stearyl alcohol, white soft paraffin and liquid paraffin.

U.S. Pat. No. 4,070,462, Ecker, issued Feb. 24, 1978, discloses a topical vehicle which includes (i) 5–15% 1,2-propanediol, 2,3-butanediol or 2-methyl-2,4, propanediol; (ii) 1–3% propylene glycol monostearate; and (iii) petrolatums and waxes to 100%.

U.S. patent application, Ser. No. 001,974, Wickett, et al., filed Jan. 8, 1979, describes compositions useful in the treatment of acne. These compositions contain benzoyl peroxide, $C_6$–$C_{14}$ primary alcohols, and a diol selected from 1,2-propanediol, 1,2-butanediol, 1,3-butanediol, and 2,3-butanediol. A foreign equivalent of this application was made available to the public July 23, 1980. See European Patent Application No. 13,459.

U.S. patent application Ser. No. 296,706, Cooper, et al., filed Aug. 27, 1981, describes compositions for topical application. These compositions described are suitable for effective delivery of lipophilic, pharmacologically active compounds using primary alcohols or various carboxylate compounds in combination with selected diols. See European Patent Application No. 43,738.

U.S. patent application Ser. No. 383,391, Cooper, filed June 1, 1982, discloses and claims a binary penetration system utilizing a diol and a cell-envelope disordering compound to aid in the penetration of 9-hydroxyethoxymethyl (and related) derivatives of 6- and 2,6-substituted purines. These purine compounds are reported to be effective in the treatment of viral infections, especially herpes, and can be administered parenterally, orally or topically. 9-(2-hydroxyethoxymethyl) guanine is disclosed as being particularly active.

1,2-propanediol ("propylene glycol") and the $C_{10}$–$C_{14}$ alcohols have been used, separately, in cosmetic and pharmaceutical formulations. In particular, propylene glycol has been described in several articles in the literature as enhancing the penetration of certain pharmacologically active agents, such as the corticosteroids. See Rosuold, J., et al., "Effect of Formulation On In Vitro Release and In Vivo Absorption of Corticosteroids from Ointments", *Medd. Novsk Favm Selsk,* 44, 21–45 (1982); see also, Anjo, D. M., et al., "Methods for Predicting Percutaneous Penetration in Man", *Percutaneous Absorption of Steroids.* pp 31–51, Academic Press, New York, N.Y. (1980).

U.S. Pat. No. 3,535,422, Cox, et al., Oct. 20, 1970, relates to stable benzoyl peroxide compositions containing organic emollients. The compositions include emollients selected from the $C_4$–$C_{20}$ aliphatic alcohols, $C_2$–$C_3$ glycols, $C_{12}$–$C_{20}$ fatty acids and their esters, and mixtures thereof.

U.S. Pat. No. 4,070,462, Ecker, issued Jan. 24, 1978, describes topical steroid compositions containing 6% propylene glycol and 1% propylene glycol monostearate.

Canadian Pat. No. 1,072,009, Sipos, issued Feb. 19, 1980, describes topical antimicrobial compositions containing $C_5$–$C_{10}$ straight chain alcohols or $C_{17}$ branched chain alcohols in which the longest chain is $C_5$–$C_{10}$.

CA 92:153,181j; describes an indomethacin ointment containing 10% propylene glycol and 1.1% diisopropanolamine.

U.S. Pat. No. 2,990,331, Neumann, et al., issued June 27, 1961, describes tetracycline compositions containing carboxylic acid alkylolamides.

H. Barnes, et al., *Br. J. Derm.* 93, 459 (1975), describe testing of fluocinonide and fluocinolone acetonide in a vehicle described as fatty alcohol propylene glycol (FAPG).

P. J. W. Ayres, et al., *Br. J. Derm.,* 99, 307 (1978), report comparative skin penetration of cortisol from commercially available cortisol ointments.

Schaaf and Gross, *Dermatologica,* 106, 357 (1953), note that unsaturated fatty acids and $C_6$–$C_{14}$ saturated fatty acids are particularly active in provoking epidermal thickening.

J. Zatz, et al., *J. Pharm. Sci.,* 67, 789 (1978), describe the effect of formulation factors on penetration of hydrocortisone through mouse skin.

S. K. Chandrasekaran, et al., *J. Pharm. Sci.,* 67, 1370 (1978), discuss the pharmacokinetics of drug permeation through human skin.

B. Idson, *Cosmetics & Toiletries,* 95, 59 (1980), states that the factors affecting drug penetration and, consequently, in most cases, effectiveness, are complex. He observes that the vehicle that provides ideal conditions for one drug may prove unsatisfactory for another. The author concludes that prediction is not simple and product suitability must be assessed by human trials. The same article indicates that Synalar Cream, a topical corticosteroid preparation, contains sorbitan monooleate and propylene glycol.

M. M. Rieger, *Cosmetics & Toiletries,* 94, 32–37 (1979) and 95, 26–38 (1980), provides a review of current literature in the area of skin penetration.

U.S. Pat. No. 4,299,826, Luedders, issued Nov. 10, 1981, describes a composition for the treatment of acne by using diisopropyl sebacate as a penetration enhancer for an erythromycin derivative in combination with an alcohol.

U.S. Pat. No. 2,990,331, Neumann, et al., issued June 27, 1961, describes the parenteral administration of tetracycline salts from a stable aqueous solution.

CA 79: 122,308, describes an electromagnetic study of n-alkyl ionic surfactants as aiding in human epidermis penetration.

SUMMARY OF THE INVENTION

The present invention relates to improved compositions and methods for the percutaneous delivery of corticosteroids to human and animal tissue and systems. The invention provides penetrating corticosteroid compositions and therapies, and is based on the use of a corticosteroid together with a binary mixture of a cell-envelope disordering compound and a diol compound formulated (and applied) in compositions which are substantially free of any polar lipids or cosolvents which interfere with steroid penetration.

The compositions of this invention comprise a safe and effective amount of a corticosteroid, together with a penetration-enhancing vehicle containing a $C_3$–$C_4$ diol, such as propylene glycol, and a cell-envelope disordering compound, such as oleic acid, said vehicle being substantially free of saturated, straight chain $C_{16}$–$C_{20}$ primary alcohols, and $C_4$–$C_{20}$ mono- or dicarboxylic acids. The compositions act to provide effective topical treatment of corticosteroid-indicated conditions by effectively delivering high levels of the steroid through the skin. These compositions can be formulated to deliver steroids at levels and rates useful in local or systemic treatment. The effectiveness of this binary mixture, designed for lipophilic anti-inflammatory actives of the nonsteroidal variety, as well as selected antivirals, is surprising in light of the dissimilar nature of the steroid active.

The invention also encompasses treatment regimens for inflammatory or other steroid-indicated conditions comprising topically administering to a human or lower animal in need of such treatment a safe and effective amount of the composition. The composition is applied at the afflicted sitis when the condition being treated is responsive to local treatment regimens.

DETAILED DESCRIPTION OF THE INVENTION

By "topical administration", as used herein, is meant directly laying on or spreading on epidermal tissue, especially outer skin or membrane, including the skin or membrane of the oral or vaginal cavities.

By "safe and effective amount", as used herein, is meant a sufficient amount of the composition to provide the desired immunosuppresive or anti-inflammatory effect and performance at a reasonable benefit/risk ratio attendant any medical treatment. Within the scope of sound medical judgment, the amount of pharmaceutical active used will vary with the particular condition being treated, the severity of the condition, the duration of the treatment, the specific compound employed, its concentration, the condition of the patient, concurrent therapies being administered, and like factors within the specific knowledge and expertise of the patient or the attending physician.

By "toxicologically- or pharmaceutically-acceptable", as used herein, is meant the steroid compounds, as well as the other compatable drugs, medicaments or inert ingredients which the term describes are suitable for use in contact with the tissues of humans and lower animals without undue toxicity, irritation, allergic response, and the like, commensurate with a reasonable benefit/risk ratio.

By the term "comprising", as used herein, is meant that various other compatible drugs and medicaments, as well as inert ingredients, occlusive agents, and cosmetic vehicles, can be conjointly employed in the compositions and processes of this invention, as long as the critical binary penetration enhancement vehicle and pharmaceutical active are used and the penetration-interfering lipids ae limited in the manner disclosed herein. The term "comprising" thus encompasses and includes the more restrictive terms "consisting of" and "consisting essentially of" which characterize the use of the essential ingredients in the manner disclosed herein.

By "afflicted situs", as used herein, is meant a localized area of inflammation or lesion, and the immediately surrounding area.

By "application situs", as used herein, is meant a site suitable for application via a mechanical sustained release device or dressing, e.g., behind the ear, on the back, leg, arm, top of the foot, etc.

By "penetration-enhancing", as used herein, is meant that the binary penetration enhancing carriers of this composition provide marked transepidermal or percutaneous delivery of an incorporated steroid, when compared to other compositions at equal chemical potential. This latter aspect is important, since varying solubilities of drugs in different vehicles will necessarily affect their transport across skin. Thus, for example, if a drug is soluble in vehicle A to the extent of 24%, and in vehicle B to the extent of 4%, if the compositions were to be compared at equal percentage concentration, rather than equal chemical potential, the lower solubility carrier will show a misleading six-fold difference in transport over the more soluble vehicle. The simplest way of assuring equal chemical potential for evaluating penetration enhancement is to use saturated solutions or solutions of equal percentage of saturation of pharmacological active in the various vehicles.

By "substantially free", as used herein, is meant that the penetration-enhancing compositions and carriers of the present invention contains less than about 3.5%, preferably less than about 1%, and most preferably less than about 0.5%, of any single or specific compound, or member of the group of compounds, described by this term.

As used herein, all percentages are by weight unless otherwise specified.

The compositions of this invention require, at a minimum, a corticosteroid active useful as an immunosuppresive or anti-inflammatory agent, a diol compound, and a cell-envelope disordering compound. The compositions of this invention may additionally contain other optional components which reduce skin irritation, or enhance their cosmetic appeal and acceptability, i.e., thickeners, pigments, and the like. The compositions must be substantially free from penetration-interfering polar lipids or polar cosolvents, particularly straight chain $C_{16}$–$C_{20}$ saturated primary alcohols, and $C_4$–$C_{20}$ mono- or dicarboxylic acids.

STEROIDS

The steroid components useful in the present invention are well-known in the pharmaceutical art. While many types of steroids may be used, including contraceptive-type steroids, corticosteroids are preferred. These are described in detail in Miller and Munro, *Drugs,* 19, 119–134 (1980); and Wolfe, *Burger's Medicinal Chemistry,* 3, 4th Ed., John Wiley and Sons, New York, N.Y., pp. 1273–1316, 917–1309 (1981); both are incorporated herein by reference. The essential steroid structure consists of 17 carbon atoms, arranged in 4 rings, 3 six-membered rings and one 5-membered ring (See Base steroid structure, below). Since this is a rigid structure, small changes in the substituents can lead to significant changes in biological activity. This is presumably the result of a change in the interaction with specific site receptors involved in protein metabolism.

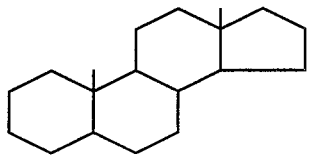

(BASE STEROID STRUCTURE)

Many valuable anti-inflammatory steroids have been developed by various modifications of the basic steroid structure. For example, the introduction of a double bond at the 1,2 position into hydrocortisone increases glucocorticoid activity by approximately 4 orders of magnitude while at the same time reducing mineralo corticoid effects. Prednisone and prednisolone are examples of such a modification.

Examples of corticosteroids useful in the present invention include, without limitation are hydroxyl-triamcinolone, alpha methyl dexamethasone, beta methyl betamethasone, beclomethansone dipropionate, betamethasone benzoate, betamethasone dipropionate, betamethasone valerate, clobetasol valerate, desonide, desoxymethasone, dexamethansone, difluorasone diacetate, diflucortolone valerate, fluadrenolone, fluclorolone acetonide, flumethasone pivalate, fluosinolone acetonide, fluocinonide, flucortine butylester, flucortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate.

Mixtures of corticosteroids, particularly any of the above corticosteroids, are also useful in the present invention.

Examples of specific corticosteroids and their customary dosage levels useful in the present invention when local treatment is desirable can be broken down into four classes:

(1) Very potent
  Beclomethasone dipropionate 0.5%
  Clobetasol propionate 0.05%
  Diflucortolone valerate 0.3%
  Fluocinolone acetonide 0.2%
(2) Potent
  Beclomethasone dipropionate 0.025%
  Betamethasone benzoate 0.025%
  Betamethasone dipropionate 0.05%
  Betamethasone valerate 0.1%
  Desonide 0.05%
  Desoxymethasone 0.25%
  Diflorasone diacetate 0.05%
  Diflucortolone valerate 0.1%
  Fluclorolone acetonide 0.025%
  Fluosinolone acetonide 0.025%
  Fluocinonide 0.05%
  Fluocortolone 0.5%
  Fluprednidene (fluprednylidene) acetate 0.1%
  Flurandrenolone 0.05%
  Halcinonide 0.1%
  Hydrocortisone butyrate 0.1%
  Triamcinolone acetonide 0.1%
(3) Moderately Potent
  Clobetasone butyrate 0.05%
  Flumethasone pivalate 0.02%
  Fluocinolone acetonide 0.01%
  Flucortin butylester 0.75%
  Flucortolone 0.2%
  Flurandrenalone 0.0125%–0.025%
  Hydrocortisone with urea 1%
(4) Mild
  Dexamethasone 0.01%
  Hydrocortisone (alcohol or acetate) 0.1%–1%
  Methylprednisolone 0.25%

Mixtures of corticosteroids are also useful in the present invention. Particularly preferred corticosteroids for use in the present invention when topical treatment is desired include triamcinolone acetonide, hydrocortisone acetate, betamethasone valerate, fluocinolone acetonide, flupamesone, and mixtures of these compounds.

Examples of specific corticosteroids useful in the present invention when systemic treatment is desired include desoxycorticosterone, fludrocortisone, hydrocortisone, betamethasone, cortisone, dexamethasone, prednisolone, prednisone, methyl prednisolone, paramethasone, triamcinolone, and mixtures of these compounds.

Compositions of the present invention contain a safe and effective amount of the corticosteroid component; preferably the compositions contain from about 0.01% to about 10%, more preferably from about 0.02% to about 5%, of corticosteroid. The compositions most preferably contain about 0.05% to about 5% of corticosteroid. Of course, the level of steroid will vary with the condition being treated, whether topical or systemic effects are desired, the surface area available for application, and the particular vehicle selected, and the method of application. Higher levels are usually required when systemic effects are desired.

VEHICLE

The vehicles of the present invention significantly enhance the penetration of the corticosteroid. They comprise, at a minimum, a diol and a cell-envelope disordering compound.

The diol compounds useful in the compositions and methods of the instant invention include 1,2-propanediol, 1,3-propanediol, 1,2-butanediol, 1,3-butanediol, 1,4-butanediol, or mixtures of these diol compounds. 1,2-propanediol and 1,2-butanediol are preferred diol compounds. 1,2-propanediol is an especially preferred diol compound.

The "cell-envelope" disordering compounds useful in the compositions and methods of the present invention include methyl laurate, oleic acid, oleyl alcohol, monoolein, and myristyl alcohol. Mixtures of these "cell-envelope" disordering compounds may also be employed. Preferred cell-envelope disordering compounds for use in the present invention include methyl laurate, oleic acid and myristyl alcohol. Methyl laurate is a particularly preferred cell-envelope disordering compound.

Binary mixtures of any of the foregoing diol compounds and cell-envelope disordering compounds, in a weight ratio of diol compound:cell-envelope disordering compound of from about 1:1 to about 500:1, provide significant enhancement of penetration for the corticosteroids described herein. A ratio of diol compound::cell-envelope disordering compound of from about 5:1 to about 100:1 is preferred, and the penetrating components are most preferably present in a ratio of about 10:1 to about 100:1. In a highly preferred embodiment, the penetrating components are present in a ratio of about 10:1 to about 50:1.

The compositions of this invention typically contain from about 10% to about 99.9%, and preferably about 15% to about 99.9%, by weight, of the penetration enhancing binary mixture of the diol compounds and cell-envelope disordering compounds, employing the ratios described above. In a highly preferred embodiment the binary mixture is present in the composition of the present invention at a level of about 50% to about 99.9% by weight.

The preferences expressed above are predicated solely upon maximizing penetration. In certain topical formulations, however, aesthetic and cosmetic qualities may be of equal or even paramount importance. Accordingly, ranges other than those described above may be preferred. In general, a composition employing a weight:weight ratio of about 1:1 to about 10:1 will not demonstrate the same degree of penetration enhancement as a system employing the same components at a weight ratio of about 10:1 to about 50:1. However, such ratios (1:1–10:1) may be preferred for certain vehicles or systems because they frequently produce better aesthetic qualities. It should be noted that while not generally providing maximum penetration, such aesthetically pleasing compositions nonetheless demonstrate a dramatic enhancement of penetration when compared to conventional or art-disclosed vehicles or systems. Compositions comprising a binary mixture at a level of about 25% to about 45% of the overall composition and employing weight: weight ratios of about 4:1 to about 6:1 provide an excellent compromise or balance of cosmetic acceptability and enhanced penetration and are accordingly preferred.

OPTIONAL COMPONENTS

In addition to the components described above, the compositions of this invention may optionally contain a cosmetically acceptable solvent. The solvent, if used, should not significantly interfere with the penetration action of the binary combination, and should preferably evapoate rapidly and completely to leave only the active components of the composition at the site of application. Preferred solvents include ethanol and isopropanol.

Water may be used as a solvet or component in the compositions of the present invention. However, simple addition of water to these compositions may cause some or all of the penetration-enhancing compounds to precipitate out. Such action in the formulation of the compositions of the present invention may significantly reduce the overall effectiveness of the system. In order to prevent this, if water is used, it is preferred that an emulsion or gel be formed. Since these compounds themselves, used alone, do not form an emulsion or gel stable enough for the intended use of the compositions, emulgents or gelling agents should therefore be employed.

Such solvents, i.e., water, ethanol or 2-propanol (isopropanol; isopropyl alcohol), may comprise from 0% to about 80% of the total composition by weight. Ethanol and 2-propanol are preferably present at a level of 0% to about 70%.

However, certain solvents, cosolvents, excipients, lipid materials and other generally acceptable components conventionally found in topical pharmaceutical compositions (other than the cell-envelope disordering compounds) should be avoided in the practice of the present invention. It is thought that such compounds compete in some fashion for the role the cell-envelope disordering compounds play, or the cite these compounds occupy, in the stratum corneum. This competition prevents the disruption or disordering of the lipids of the stratum corneum by the cell-envelope disordering compounds. Some of these compounds may also compete with the lipids of the stratum corneum for the cell-envelope disordering compound and the cell-envelope disordering compound will preferentially partition into such lipid-like compounds in the vehicle rather than the lipids of the stratum corneum. Such selective competition will also prevent lipid disordering or disruption by the cell-envelope disordering compound and, accordingly, the steroid cannot be aided in penetrating. Thus, such compounds should be avoided when formulating the compositions of the present invention. If used, such compounds should generally be used as sparingly as possible, far below art-established levels.

For example, hydrocarbons such as liquid petrolatum (mineral oil, liquid paraffin, paraffin oil), white petrolatum, yellow petrolatum, paraffin, microcrystalline wax, and ceresin are all known to be useful as hydrophobic vehicles or structural matrix formers in topical pharmaceutical formulations. However, all of these excipients are capable of significantly interfering with the penetration enhancing abilities of the present invention. It is thought that these compounds inhibit the ability of the cell-envelope disordering compound to effectively disrupt the intercellular lipid structure of stratum corneum by preventing the cell-envelope disordering compound from effectively reaching the lipids of the stratum corneum, possibly by selective competition for the cell-envelope disordering compound. While a certain level of such ingredients can be tolerated in a system which is otherwise particularly effective, in a preferred embodiment of the present invention such ingredients are limited to less than about 10%, and preferably less than about 5%.

Certain straight chain, saturated $C_{16}$–$C_{20}$ normal fatty alcohols should also be avoided. Cetyl alcohol and stearyl alcohol are extremely common, ubiquitous ingredients in topical formulations. Both of these alcohols are capable of significant interference with the penetration enhancement of the present vehicle. These alcohols, as well as the $C_{18}$ saturated normal alcohol, are likely to retard the penetration enhancing abilities of the systems of the present invention. Accordingly, in a preferred embodiment, the compositions of the present invention are substantially free of such compounds, i.e., any particular compound should be present at a level of less than 3.5%, and more preferably at a level less than 1% by weight of the entire composition. In a highly preferred embodiment the compositions of the present invention contain less than 0.5% of any specific member of said alcohol group.

Certain fatty acids are also capable of gross interference with steroid penetration. These acids include the straight chain $C_4$–$C_{20}$ saturated monocarboxylic and dicarboxylic acids. Octanoic and decanoic acid are particularly harmful to the vehicles of the present system. In a preferred embodiment, the compositions of the present invention are substantially free of these acids, i.e., contain less than about 3.5% of any particular member of $C_4$–$C_{20}$ saturated monocarboxylic and dicarboxylic acid, and more preferably less than about 1% of said acids by weight of the entire composition. In a highly preferred embodiment the compositions of the present invention contain less than 0.5% of any specific member of said acid group.

The compositions of the present invention may additionally contain other adjunct components conventionally found in pharmaceutical compostions, not recited above, at their art-established usage levels. Thus, for example, the compositions may contain additional compatible phramaceutically-active materials for combination therapy (such as antimicrobials, antipruritics, astringents, local anesthetics, or non-steroidal anti-inflammatory agents), or may contain materials useful in physically formulating various dosage forms of the present invention, such as excipients, dyes, perfumes, fragrances, preservatives, anti-oxidants, opacifiers, thickening agents and stabilizers. Such materials, when added, should not unduly interfere with the penetration enhancement of these compositions. Such formula modifications to improve cosmetic acceptability are well within the skill of workers in the cosmetic and dermatological arts and, by themselves, constitute no part of the present invention.

All optional components should be selected to prevent substantial interference with the penetration ability of the composition.

It can be see from the foregoing that the compositions of the present invention admit of considerable variation, so long as the critical components of corticosteroid, diol compound, and cell-envelope disordering compound is present within the ranges indicated above and the stated penetration interfering components are minimized.

METHOD TO USE

It will be appreciated that this invention provides a method for treating and preventing conditions which respond to either local or systemic activity of corticosteroids. Such conditions may be responsive to either the immunosuppresive or anti-inflammatory action of such steroids. When local treatment is desired, the compositions of the present invention are applied to the afflicted situs. When systemic treatment is desired, the compositions of the present invention are applied to an application situs, preferably from a sustained release film, web, bandage or device. Such devices are well-known in the art, and examples of such films, webs, bandages, devices, and the like can be found in Johnson, J. C., et al., *Sustained Release Medications, Chemical Technology Review* No. 177, Noyes Data Corporation, Park Ridge, N.J., pp. 82-113, (1980), incorporated herein by reference. When both local and systemic treatments are indicated or desired, the compositions of the present invention can be applied at the afflicted situs, an application situs, or both. Accordingly, this invention provides a method for treating and preventing nonendocrine immunologic or rheumatic diseases such as rheumatoid arthritis, rheumatic fever, disseminated lupus erythematosus, hypersensitivity reactions such as bronchial asthma, serum sickness, anaphylaxis, bee stings, angioneurotic edema and hay fever, hemolytic enemia, drug reactions and agranulcytosis. The present invention also provides a method for treating diseases of the liver such as chronic active hepatitis. Certain neurological conditions such as cerebral edema, or an increase in intracranial pressure, may also be treated. The present invention further provides a method for treating and preventing inflammatory conditions such as ulcerative colitis, dermatitis (atopic, eczematoid, exfoliative, stasis, nummular, contact, or seborrheic), pemfhigus, gout and other inflammations of skin or mucous membranes caused by chemical, thermal, mechanical or radiant agents. In addition, the present invention may be formulated and used in a veterinary context, for example in the treatment of dermatological disorders characterized by inflammation and dry or exudative dermatitis, eczematous dermatitis, contact dermatitis, seborrheic dermatitis, and as an adjunct in the treatment of dermatitis due to parasitic infestation.

It will be appreciated that the number and severity of side effects produced by systemic corticosteroid therapy are significantly increased when compared with localized therapy. Thus, the decision to use corticosteroids for systemic treatment requires a clear definition of the benefits to be gained by such treatment, an identification of the risks the subject may encounter, so that informed overall assessment may be made. The risks attendant the systemic use of corticosteroids include abnormal sodium reabsorption and potassium excretion. This interference with the two important monovalent ions may result in hypokalemic alkalosis, edema, hypertension and other abnormalities associated with electrolyte imbalances. Corticosteroids, when delivered systemically, may also suppress the natural healing process of injuries, especially those that cause a break in the integument. The immunosuppresive properties of corticosteroids, the very property which makes them valuable in the treatment of immunologically mediated disease, can result in a compromise of the subject's ability to fight infection. They can also mask the symptoms of some infections, thus preventing or delaying diagnosis and treatment. Further side effects include abnormal function within the gastrointestinal, cardiovascular, endocrine and central nervous systems. These may occur in any subject receiving a supraphysiologic concentration of corticosteroid hormones or their synthetic equivalents. In general, the frequency and severity of such side effects are proportional to the dose given, and the duration of treatment. When either the amount per dose, or the period of time over which therapy is given is increased, an increase in side effects can also be anticipated.

Accordingly, in actual clinical practice, two rules become paramount when systemic corticosteroid therapy is to be administered in the treatment of any condition or episode:

(1) the period of administration must be as short as possible; and (2) the delivered dosage must be the smallest one that will achieve the desired effect.

When the therapy which calls for single administration is indicated, the single administration can be viewed as inocuous in character. Short courses of systemic steroid therapy of substantial doses may be proper in conditions which are not life-threatening assuming the absence of specific contraindications. However, it is generally accepted that courses of long-term therapy at a high dosage should be reserved only for life-threatening disease. This rule is occassionally violated justifiably when the patient is threatened with significant and permanent disability. See Goodman and Gilman, *The Pharmacological Basis of Therapeutics,* Macmillan Publishing Company, Inc., pp. 1497–1500 (1975), incorporated herein by reference.

In summary, the individual dosage must be particularly suited to the individual condition being treated when using the compositions of the present invention for systemic treatment as well as localized treatment when systemic effects are possible side-effects of such localized treatment.

The compositions of this invention are typically applied one to six times daily to the afflicted situs when topical treatment is desired. When systemic effcts are also desired, or when it is desired to reduce the chance of the spread of infection, the compositions of this invention are applied to larger areas, more frequently, or from a mechanical sustained release device or dressing.

Topical treatment regimens according to the practice of this invention comprise applying the compositions herein directly to the skin, i.e, at the afflicted situs or the application situs. The compositions may also be formulated for use in the oral or vaginal cavities. The rate of application and duration of treatment will, of course, depend on many factors. A typical safe and effective usage rate for topical treatment is about 1 mg of the total topical composition per square centimeter of skin to about 10 mg of total topical composition per square centimeter of skin per application and about 1 mg of the total topical composition to about 100 mg of the total topical composition per square centimeter of skin when systemic, or local and systemic, effects or treatment are desired. The skilled artisan will appreciate that this application rate will vary with the desired effect (systemic, local, or systemic and local), the condition being treated, its progress and response, the area involved, the severity and nature of the condition being treated, the nature of the actives or carriers, the presence or absence of penetration-interfering solvents, cosolvents, excipients and lipids, the physical condition of the patient, concurrent therapies being administered, the concentration of the actives or carriers being used, as well as other factors within the particular knowledge of the patient and/or physician within the scope of sound medical judgment. However, usage rates of up to 500 mg of total composition per square centimeter of skin may be used when the composition is used as an occlusive dressing. Even larger rates may be employed when a mechanical sustained delivery device or dressing is used.

The compositions can be applied once every twenty-four hours to about twenty-four times every twenty-four hours. Application intervals of every 4 hours to every 12 hours are preferred. A treatment regimen of application every 6 hours is particularly preferred because it minimizes the amount of steroid which is applied at one time while reducing the inconvenience of frequent applications. However, any treatment regimen which allows a safe and effective amount of steroid to reach the afflicted situs or the bloodstream can be employed while using the compositions of this invention. For possibly compatible and related topical compositions and treatment regimens, see concurrently filed U.S. Patent Applications entitled "Improved Penetrating Topical Pharmaceutical Compositions Containing 1-Dodecylazacycloheptan-2-One", Cooper, Ser. No. 506,275, filed June 21, 1983; and "Penetrating Topical Pharmaceutical Compositions Containing N-(2-Hydroxyethyl)pyrrolidone", Cooper, Ser. No. 506,273, filed June 21, 1983; both expressly incorporated herein by reference.

The following are nonlimiting examples of the composition of the present invention. They are conventionally formulated by mixing all components thoroughly.

EXAMPLE 1—PART A

| Composition I | |
|---|---|
| Triamcinolone acetonide (Triamcinolone hereafter) | 1.0% |
| Propylene Glycol (1,2-propanediol) | 95.0% |
| Methyl laurate | 4.0% |
| Composition II | |
| Hydrocortisone acetate | 1.0% |
| Propylene Glycol (1,2-propanediol) | 94.0% |
| Oleic Acid | 5.0% |
| Composition III | |
| Betamethasone valerate | 0.5% |
| Propylene Glycol (1,2-propanediol) | 93.5% |
| Oleyl alcohol | 6.0% |
| Composition IV | |
| Fluocinolone acetonide | 0.5% |
| Propylene Glycol (1,2-propanediol) | 94.5% |
| Monoolein | 5.0% |
| Composition V | |
| Flupamesone | 0.5% |
| Propylene Glycol (1,2-propanediol) | 97.5% |
| Myristyl alcohol | 2.0% |
| Composition VI | |
| Triamcinolone | 0.5% |
| 1,2-butanediol | 95.5% |
| Methyl laurate | 4.0% |
| Composition VII | |
| Triamcinolone | 0.5% |
| 1,3-butanediol | 97.5% |
| Methyl laurate | 2.0% |
| Composition VIII | |
| Hydrocortisone acetate | 0.25% |
| 1,2-butanediol | 97.75% |
| Oleic acid | 2.0% |
| Composition IX | |
| Hydrocortisone acetate | 2.0% |
| 1,3-butanediol | 93.0% |
| Oleic acid | 5.0% |
| Composition X | |
| Betamethasone valerate | 2.0% |
| 1,2-butanediol | 93.0% |
| Oleyl alcohol | 5.0% |
| Composition XI | |
| Fluocinolone acetonide | 5.0% |
| 1,2-butanediol | 92.0% |
| Monoolein | 3.0% |
| Composition XII | |
| Flupamesone | 1.0% |
| Hydrocortisone Acetate | 1.0% |
| Propylene glycol (1,2-propanediol) | 93.0% |
| Myristyl alcohol | 5.0% |
| Composition XIII | |
| Desoxycorticosterone | 5.0% |
| Propylene Glycol (1,2 propanediol) | 90.0% |
| Oleic acid | 5.0% |
| Composition XIV | |
| Prednisolone | 5.0% |
| Propylene Glycol (1,2-propanediol) | 91.0% |
| Myristyl alcohol | 4.0% |
| Composition XV | |
| Prednisone | 2.0% |
| 1,2-butanediol | 54.0% |
| Oleic acid | 4.0% |
| ethanol | 40.0% |

-continued

| Composition XVI | |
|---|---|
| Methyl prednisolone | 4.0% |
| 1,3-butanediol | 55.0% |
| Oleyl alcohol | 1.0% |
| isopropanol | 40.0% |

The following are nonlimiting examples of the methods of the present invention.

EXAMPLE 1—PART B

Composition I is applied to a human afflicted with dermatitis at the afflicted situs at a rate of 5 mg of composition per square centimeter of skin three times daily for a period of 5 days. Complete elimination of inflammation is noted after 48 hours. Substantially similar results are obtained when the composition is replaced by compositions II, III, IV or V of Example 1.

PENETRATION STUDIES

EXAMPLES 2-31

The following Penetration Studies demonstrate the penetration-enhancing capabilities of the compositions and methods of the present invention. These nonlimiting Examples demonstrate the ability of the compositions of the present invention to enhance penetration of triamcinolone or hydrocortisone when compared to a propylene glycol or a propylene glycol-containing vehicle formulated without the presence of the critical cell-envelope disordering compound.

The following Penetration Studies were carried out in the following manner. Human skin (heat-separated or dermatomed abdominal epidermis, taken at autopsy, or excised, full thickness hairless mouse skin) is placed in a standard Franz diffusion apparatus (Crown Glass Company, Somerville, NJ) in a horizontal position between a lower, capped diffusion cell and an upper, open cell. A normal saline solution is added to the lower diffusion cell, abutting the subcutaneous side of the skin. The test composition (comprising a solution of active or actives added to the carrier at the indicated formulation in a conventional manner by thoroughly mixing) is added to the diffusion cell abutting the epidermal side of the skin at the levels indicated.

This cell assembly is kept at a constant temperature of about 31° C. At appropriate or desired intervals (these are the time designations given in the following examples) each diffusion cell assembly is opened and the diffusate from the cell abutting the subcutaneous side of the skin is withdrawn. Drug actives in a diffusate is measured using standard analytical techniques. Each trial is run on a separate sample of skin.

In the following examples, (*) indicates that human skin was selected for this trial, and (**) indicate that hairless mouse skin was selected. All ratios represented by A/B, or A/B/C, and all percentages, are by weight. The compounds described as $C_{12-18}OH$ are the straight chain, saturated, normal alcohols. EtOH is ethanol. The term mcg=microgram.

EXAMPLE 2

| Vehicle | mcg/cm$^2$ (0-24 hrs.)* |
|---|---|
| .5% Triamcinolone in a vehicle of Propylene Glycol | 0.4 |
| .5% Triamcinolone in a vehicle of 98% Propylene Glycol + 2% $C_{14}OH$ | 11 |
| .5% Triamcinolone in a vehicle of 95% Propylene Glycol + 5% Oleic Acid | 172 |

EXAMPLE 3

| Vehicle | mcg/cm$^2$ (0-8 hrs.)** |
|---|---|
| .5% Triamcinolone in a vehicle of Propylene Glycol | 0.35 |
| .5% Triamcinolone in a vehicle of 95% Propylene Glycol + 5% Oleic Acid | 45 |

EXAMPLE 4

| Vehicle | mcg/cm$^2$ (0-8 hrs.)** |
|---|---|
| .5% Triamcinolone in a vehicle of Propylene Glycol | 0.21 |
| .1% Triamcinolone in a vehicle of Oleic Acid | 1.8 |
| .5% Triamcinolone in a vehicle of 99% Propylene Glycol + 1% Oleic Acid | 23 |
| .5% Triamcinolone in a vehicle of 95% Propylene Glycol + 5% Oleic Acid | 46 |
| .4% Triamcinolone in a vehicle of 75% Propylene Glycol + 25% Oleic Acid | 39 |

EXAMPLE 5

| Vehicle | mcg/cm$^2$ (0-6 hrs.)** |
|---|---|
| .1% Triamcinolone in a vehicle of 20/80 Propylene Glycol/EtOH | 0.17 |
| .1% Triamcinolone in a vehicle of 15/5/80 Propylene Glycol/Oleic Acid/EtOH | 2.65 |
| .1% Triamcinolone in a vehicle of 15/5/80 Propylene Glycol/Methyl laurate/EtOH | 2.73 |
| .1% Triamcinolone in a vehicle of 15/5/80 Propylene Glycol/$C_{14}OH$/EtOH | 1.40 |
| .1% Triamcinolone in a vehicle of 15/5/80 Propylene Glycol/Monoolein/EtOH | 0.49 |
| .1% Triamcinolone in a vehicle of 15/5/80 Propylene Glycol/Azone/EtOH | 1.87 |

EXAMPLE 6

| Vehicle | mcg/cm$^2$ (0-4 hrs.)** |
|---|---|
| .1% Triamcinolone in a vehicle of 20/80 Propylene Glycol/EtOH | 0.94 |
| .1% Triamcinolone in a vehicle of 15/5/80 Propylene Glycol/Oleic Acid/EtOH | 6.4 |
| .1% Triamcinolone in a ehicle of 15/5/80 Propylene Glycol/Linoleic Acid/EtOH | 5.4 |
| .1% Triamcinolone in a vehicle of 15/5/80 Propylene Glycol/Oleyl Alcohol/EtOH | 3.1 |
| .1% Triamcinolone in a vehicle of 15/5/80 Propylene Glycol/Linoleyl Alcohol/EtOH | 5.3 |

EXAMPLE 7

| Vehicle | mcg/cm² (0–70 hrs.)* |
|---|---|
| .1% Triamcinolone in a vehicle of 20/80 Propylene Glycol/EtOH | .29 |
| .1% Triamcinolone in a vehicle of 15/5/80 Propylene Glycol/Methyl Laurate/EtOH | 1.6 |
| 1% Hydrocortisone in a vehicle of 20/80 Propylene Glycol/EtOH | 2.8 |
| 1% Hydrocortisone in a vehicle of 15/5/80 Propylene Glycol/Methyl Laurate/EtOH | 5.4 |
| 1% Hydrocortisone in a vehicle of 15/5/80 Propylene Glycol/Oleic Acid/EtOH | 13.0 |
| 1% Hydrocortisone in a vehicle of 15/5/80 Propylene Glycol/$C_{14}OH$/EtOH | 8.8 |

EXAMPLE 8

The following Example demonstrates the dramatic reduction in penetration that takes place when the penetration-inhibiting compound described herein are added to compositions of the present invention.

| Vehicle | mcg/cm² (0–72 hrs.)* |
|---|---|
| 1% Triamcinolone in a vehicle of Propylene Glycol | .1 |
| 1% Triamcinolone in a vehicle of 98% Propylene Glycol + 2% $C_{14}OH$ | 30 |
| 1% Triamcinolone in a vehicle of 94% Propylene Glycol + 2% $C_{14}OH$ + 4% Octanoic Acid | 15 |

As can be seen from this example, the addition of a proscribed compound such as straight chain, normal $C_8$ monocarboxylic acid (octanoic acid), reduces penetration by 50%. Substantially similar results occur with addition of decanoic acid, cetyl alcohol or stearyl alcohol.

EXAMPLE 9

| Vehicle | mcg/cm² (24 hrs.)* |
|---|---|
| .1% Triamcinolone in Propylene Glycol vehicle | 23 |
| .1% Triamcinolone in a vehicle of Propylene Glycol + 3% Oleic Acid | 72 |
| .1% Triamcinolone in a vehicle of Propylene Glycol + 3% $C_{12}OH$ | 56 |
| .1% Triamcinolone in a vehicle of Propylene Glycol + 3% $C_{14}OH$ | 36 |
| .1% Triamcinolone in a vehicle of Propylene Glycol + 3% $C_{16}OH$ | 14 |
| .1% Triamcinolone in a vehicle of Propylene Glycol + 3% $C_{18}OH$ | 20 |
| .1% Triamcinolone in a vehicle of Propylene Glycol + 3% Oleyl Alcohol | 56 |
| .1% Triamcinolone in a vehicle of Propylene Glycol/PEG 400 | 6 |

EXAMPLE 10

| Component | mcg/cm² | mcg/cm² @24 hrs. | mcg/cm²* @48 hrs. |
|---|---|---|---|
| Triamcinolone | 0.1% | 11.2 | 20.8 |
| Methyl Laurate | 5.0% | | |
| Propylene Glycol | 25.0% | | |
| EtOH | 30.0% | | |
| Carbopol 934[1] | 1.0% | | |
| TEA (triethanol amine) | 0.3% | | |
| Tween 80[2] | 0.2% | | |
| Water qs | 38.4% | | |

[1] Carbopol 934 is a polyacrylic acid polymer available from B.F. Goodrich
[2] Tween 80 is a nonionic, liquid sorbitan monooleate available from ICI Americas

EXAMPLE 11

| Component | mcg/cm² | mcg/cm²* @24 hrs. | mcg/cm²* @48 hrs. |
|---|---|---|---|
| Triamcinolone | 0.1% | 12.5 | 37.0 |
| Oleic Acid | 2.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 41.4% | | |

EXAMPLE 12

| Component | mcg/cm² | mcg/cm²* @24 hrs. | mcg/cm²* @48 hrs. |
|---|---|---|---|
| Triamcinolone | 0.1% | 20.7 | 50.9 |
| Oleic Acid | 4.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 39.4% | | |

EXAMPLE 13

| Component | mcg/cm² | mcg/cm²* @24 hrs. | mcg/cm²* @48 hrs. |
|---|---|---|---|
| Hydrocortisone | 1.0% | 56.3 | 104.7 |
| Methyl Laurate | 5.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 37.5% | | |

EXAMPLE 14

| Component | mcg/cm² | mcg/cm²* @24 hrs. | mcg/cm²* @48 hrs. |
|---|---|---|---|
| Hydrocortisone | 1.0% | 42.5 | 91.6 |
| Oleic Acid | 2.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 40.5% | | |

EXAMPLE 15

| Component | mcg/cm² | mcg/cm²* | |
|---|---|---|---|
| | | @24 hrs. | @48 hrs. |
| Hydrocortisone | 1.0% | 51.8 | 129.6 |
| Oleic Acid | 4.0% | | |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 38.5% | | |

EXAMPLE 16

| Component | mcg/cm² | mcg/cm²* | |
|---|---|---|---|
| | | @24 hrs. | @48 hrs. |
| Hydrocortisone | 1.0% | 53.9 | 136.7 |
| Methyl Laurate | 5.0% | | |
| 1-(2-hydroxyethyl)-aza-cyclopentan-2-one | 20.0% | | |
| EtOH | 30.0% | | |
| Carbopol 934 | 1.0% | | |
| TEA | 0.3% | | |
| Tween 80 | 0.2% | | |
| Water qs | 42.5% | | |

EXAMPLE 17

| Component | mcg/cm² | mcg/cm²* | |
|---|---|---|---|
| | | @24 hrs. | @48 hrs. |
| Triamcinolone | 0.1% | 1.69 | 4.31 |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 43.4% | | |

EXAMPLE 18

| Component | mcg/cm² | mcg/cm²* | |
|---|---|---|---|
| | | @24 hrs. | @48 hrs. |
| Hydrocortisone | 1.0% | 5.96 | 12.7 |
| Propylene Glycol | 25.0% | | |
| EtOH | 30.0% | | |
| Carbopol 934 | 1.0% | | |
| TEA | 0.3% | | |
| Tween 80 | 0.2% | | |
| Water qs | 42.5% | | |

EXAMPLE 19

| Component | mcg/cm² | mcg/cm²* | |
|---|---|---|---|
| | | @24 hrs. | @48 hrs. |
| Hydrocortisone | 1.0% | 5.71 | 18.8 |
| 1-(2-hydroxyethyl)aza-cyclopentan-2-one | 20.0% | | |
| EtOH | 30.0% | | |
| Carbopol 934 | 1.0% | | |
| TEA | 0.3% | | |
| Tween 80 | 0.2% | | |
| Water qs | 47.5% | | |

EXAMPLE 20

| Component | mcg/cm² | mcg/cm²* | |
|---|---|---|---|
| | | @24 hrs. | @48 hrs. |
| Triamcinolone | 0.1% | 1.44 | 5.75 |
| Propylene Glycol | 25.0% | | |
| EtOH | 74.9% | | |

EXAMPLE 21

| Component | mcg/cm² | mcg/cm²* | |
|---|---|---|---|
| | | @24 hrs. | @48 hrs. |
| Hydrocortisone | 1.0% | 6.48 | 18.3 |
| Propylene Glycol | 24.5% | | |
| EtOH | 74.5% | | |

EXAMPLE 22

| Vehicle | mcg/cm²(0–48 hrs.)* |
|---|---|
| .5% Triamcinolone in a vehicle of Propylene Glycol | .056 |
| .1% Triamcinolone in a vehicle of Oleic Acid | .92 |
| 4.5% Triamcinolone in a vehicle of Azone | .92 |
| .6% Triamcinolone in a vehicle of 50/50 Oleic Acid/Azone | .45 |
| .5% Triamcinolone in a vehicle of Propylene Glycol + 5% Oleic Acid | 63.0 |
| .5% Triamcinolone in a vehicle of Propylene Glycol + 5% Azone | 8.4 |

EXAMPLE 23

| Vehicle | mcg/cm²(0–4 hrs.)** |
|---|---|
| 1% Triamcinolone in a vehicle of Propylene Glycol | .14 |
| 7.8% Triamcinolone in a vehicle of Azone | 8.5 |
| .05% Triamcinolone in a vehicle of Oleic Acid | .81 |
| .7% Triamcinolone in a vehicle of 50/50 Azone/Oleic Acid | 1.5 |
| 1% Triamcinolone in a vehicle of Propylene Glycol + 4% Azone | 8.2 |
| 1% Triamcinolone in a vehicle of Propylene Glycol + 4% Oleic Acid | 123.0 |

EXAMPLE 24

| Vehicle | mcg/cm² (0–22 hrs)** |
|---|---|
| 1% Triamcinolone in a vehicle of Propylene Glycol | 2.45 |
| 7.8% Triamcinolone in a vehicle of Azone | 77 |
| .05% Triamcinolone in a vehicle of Oleic Acid | 11 |
| .7% Triamcinolone in a vehicle of 50/50 Azone/Oleic Acid | 14.8 |
| 1% Triamcinolone in a vehicle of Propylene Glycol + 4% Azone | 147 |
| 1% Triamcinolone in a vehicle of Propylene Glycol + 4% Oleic Acid | 254 |

EXAMPLE 25

| Vehicle | mcg/cm$^2$(0–68 hrs.)* |
|---|---|
| 1% Triamcinolone in a vehicle of Propylene Glycol | .082 |
| 7.8% Triamcinolone in a vehicle of Azone | .6 |
| .05% Triamcinolone in a vehicle of Oleic Acid | .089 |
| .7% Triamcinolone in a vehicle of 50/50 Oleic Acid/Azone | .22 |
| 1% Triamcinolone in a vehicle of Propylene Glycol + 4% Oleic Acid | 10.5 |
| 1% Triamcinolone in a vehicle of Propylene Glycol + 4% Azone | 2.1 |

EXAMPLE 26

The following Skin Penetration Study demonstrates the dramatic increase in penetration of a pharmaceutically-active agent (here Triamcinolone) when the binary combination of diol+Azone is employed, when compared to a vehicle containing just Azone, or just the diol, and a compatable volatile solvent. The following penetration study further demonstrates the criticality of the levels required by the present invention.

| Vehicle | mcg/cm$^2$ (24 hrs.)* |
|---|---|
| 0.1% Triamcinolone in a vehicle of 95/5 Ethanol/Azone | .85 |
| 0.1% Triamcinolone in a vehicle of 85/10/5 Ethanol/Propylene Glycol/Azone | .85 |
| 0.1% Triamcinolone in a vehicle of 75/20/5 Ethanol/Propylene Glycol/Azone | 1.5 |
| 0.1% Triamcinolone in a vehicle of 55/40/5 Ethanol/Propylene Glycol/Azone | 3.0 |
| 0.1% Triamcinolone in a vehicle of 75/20/5 Ethanol/Propylene Glycol/Oleic Acid | 5.2 |
| 0.1% Triamcinolone in a vehicle of 80/20 Ethanol/Propylene Glycol | 0.37 |

EXAMPLE 27

| Vehicle | mcg/cm$^2$(0–48 hrs.)* |
|---|---|
| .1% Triamcinolone in a vehicle of 20/80 Propylene Glycol/EtOH | .12 |
| .1% Triamcinolone in a vehicle of 20/80 Pyrrolidone/EtOH | 3.5 |
| .1% Triamcinolone in a vehicle of 15/5/80 Propylene Glycol/Oleic Acid/EtOH | 5.4 |
| .1% Triamcinolone in a vehicle of 15/5/80 Pyrrolidone/Oleic Acid/EtOH | 9.9 |

EXAMPLE 28

| Vehicle | mcg/cm$^2$(0–50 hrs.)* |
|---|---|
| 1% Triamcinolone in a vehicle of 20/80 Propylene Glycol/EtOH | .8 |
| 1% Triamcinolone in a vehicle of 20/80 Hydroxyethylpyrrolidone/EtOH | 1.1 |
| 1% Triamcinolone in a vehicle of 20/80 Pyrrolidone/EtOH | 3.4 |
| 1% Triamcinolone in a vehicle of 15/5/80 Propylene Glycol/Oleic Acid/EtOH | 3.3 |
| 1% Triamcinolone in a vehicle of 15/5/80 Pyrrolidone/Oleic Acid/EtOH | 5.9 |
| 1% Triamcinolone in a vehicle of 15/5/80 Hydroxyethylpyrrolidone/Oleic Acid/EtOH | 11.6 |

EXAMPLE 29

| Vehicle | mcg/cm$^2$ (0–65 hrs.)* |
|---|---|
| .1% Triamcinolone in a vehicle of 20/80 Propylene Glycol/EtOH | .27 |
| .1% Triamcinolone in a vehicle of 15/5/80 Propylene Glycol/Methyl laurate/EtOH | 1.5 |
| .1% Triamcinolone in a vehicle of 20/80 Hydroxyethylpyrrolidone/EtOH | .29 |
| .1% Triamcinolone in a vehicle of 15/5/80 Hydroxyethylpyrrolidone/Methyl laurate/EtOH | 3.6 |
| .1% Triamcinolone in a vehicle of 20/80 Hydroxypropylpyrrolidone/EtOH | .10 |
| .1% Triamcinolone in a vehicle of 15/5/80 Hydroxypropylpyrrolidone/Methyl laurate/EtOH | .81 |
| .1% Triamcinolone in a vehicle of 20/80 Methyl Pyrrolidone/EtOH | 1.3 |
| .1% Triamcinolone in a vehicle of 15/5/80 Methyl Pyrrolidone/Methyl laurate/EtOH | 3.4 |

EXAMPLE 30

| Vehicle | mcg/cm$^2$(0–48 hrs.)* |
|---|---|
| .1% Hydrocortisone in a vehicle of 20/80 Propylene Glycol/EtOH | 7.5 |
| 1% Hydrocortisone in a vehicle of 15/5/80 Propylene Glycol/Methyl laurate/EtOH | 17.0 |
| 1% Hydrocortisone in a vehicle of 15/5/80 Propylene Glycol/Oleic Acid/EtOH | 19.0 |
| 1% Hydrocortisone in a vehicle of 20/80 Hydroxyethylpyrrolidone/EtOH | 14.0 |
| 1% Hydrocortisone in a vehicle of 15/5/80 Hydroxyethylpyrrolidone/Oleic Acid/EtOH | 120.0 |

EXAMPLE 31

| Vehicle | mcg/cm$^2$(0–48 hrs.)* |
|---|---|
| 1% Hydrocortisone in a vehicle of 20/80 Propylene Glycol/EtOH | 7.6 |
| 1% Hydrocortisone in a vehicle of 15/5/80 Propylene Glycol/Methyl laurate/EtOH | 33.0 |
| 1% Hydrocortisone in a vehicle of 20/80 Hydroxyethylpyrrolidone/EtOH | 8.3 |
| 1% Hydrocortisone in a vehicle of 15/5/80 Hydroxyethylpyrrolidone/Oleic Acid/EtOH | 124.0 |

EXAMPLE 32

| Component | % w/w |
|---|---|
| Hydrocortisone | 0.5 |

-continued

| Component | % w/w |
|---|---|
| Methyl laurate | 5.0 |
| Propylene glycol | 25.0 |
| Polysorbate 80 | 0.2 |
| Carbopol 934P | 1.5 |
| Disodium EDTA | 0.1 |
| Titanium Dioxide | 0.1 |
| 2.5% aqueous NaOH | 1.5 |
| Sorbic acid | 0.1 |
| Distilled water | 66.0 |
| | 100.00 |

The above composition is applied at the afflicted situs of a human afflicted with dermatitis at a rate of 5 mg of composition/cm$^2$ of skin three times daily for a period of five days. A significant reduction of inflammation is noted after 48 hours.

Substantially similar results are obtained when the hydrocortisone in the above composition is replaced, in whole or in part, with triamcinolone, betamethasone valerate, fluocinolone, acetonide, flupamesone, and mixtures thereof.

Likewise, substantially similar results are obtained if the methyl laurate is replaced, in whole or in part, by oleic acid, oleyl alcohol, monoolein, myristyl alcohol, or mixtures therof.

What is claimed is:

1. A penetration-enhancing pharmaceutical composition for topical application, comprising:
   (a) a safe and effective amount of a pharmaceutically-active corticosteroid;
   (b) 0% to about 80% by weight of a solvent selected from the group consisting of water, ethanol or 2-propanol; and
   (c) about 10% to about 99.9% by weight of a penetration-enhancing carrier consisting essentially of:
      (i) a diol selected from the group consisting of 1,2-propanediol, 1-2,-butanediol, 1,3-butanediol, 2,3-butanediol, or mixtures thereof, and
      (ii) a cell-envelope disordering compound selected from the group consisting of methyl laurate, oleic acid, myristyl alcohol, or mixtures thereof;
   wherein said diol and said cell-envelope disordering compound are present in a ratio of diol:cell-envelope disordering compound of from about 1:1 to about 500:1 by weight; and wherein said penetration-enhancing composition is substantially free from any single member of the $C_{16}$–$C_{20}$ straight chain, saturated normal fatty alcohols, and $C_4$–$C_{20}$ straight chain, saturated mono- or dicarboxylic acids.

2. A composition according to claim 1 wherein the cell-envelope disordering compound is methyl laurate.

3. A composition according to claim 1 wherein the cell-envelope disordering compound is oleic acid.

4. A composition according to claim 1 wherein the cell-envelope disordering compound is myristyl alcohol.

5. A composition according to claim 1 wherein the level of any specific member of the $C_{16}$–$C_{20}$ straight chain, saturated normal fatty alcohols, and $C_4$–$C_{20}$ straight chain, saturated mono- or dicarboxylic acids is less than about 3.5% by weight.

6. A composition according to claim 5 wherein the level of any specific member of the $C_{16}$–$C_{20}$ straight chain, saturated normal fatty alcohols, and $C_4$–$C_{20}$ straight chain, saturated mono- or dicarboxylic acids is less than about 1% by weight.

7. A composition according to claim 1, which is substantially free from octanoic acid, decanoic acid, cetyl alcohol and stearyl alcohol.

8. A penetration-enhancing pharmaceutical composition for topical application, comprising:
   (a) about 0.05% to about 5%, by weight of a corticosteroid selected from the group consisting of triamcinolone acetonide, hydrocortisone acetate, betamethasone valerate, fluocinolone acetonide, flupamesone, or mixtures thereof;
   (b) 0% to about 80% by weight of a solvent selected from the group consisting of water, ethanol or 2-propanol; and
   (c) about 10% to about 99.9% by weight of a penetration-enhancing carrier consisting essentially of:
      (i) a diol selected from the group consisting of 1,2-propanediol, 1,2-butanediol, or mixtures thereof;
      (ii) a cell-envelope disordering compound selected from the group consisting of methyl laurate, oleic acid, myristyl alcohol, or mixtures thereof;
   wherein said diol and said cell-envelope disordering compound are present in a ratio of diol:cell-envelope disordering compound of from about 10:1 to about 100:1 by weight; and wherein said penetration-enhancing composition is substantially free from any specific member of the $C_{16}$–$C_{20}$ straight chain, saturated normal fatty alcohols, and $C_4$–$C_{20}$ straight chain, saturated mono- or dicarboxylic acids.

9. A composition according to claim 8 wherein the diol compound is 1,2-propanediol.

10. A composition according to claim 8 wherein the diol compound is 1,2-butanediol.

11. A composition according to claim 8 wherein the cell-envelope disordering compound is oleic acid.

12. A composition according to claim 8 wherein the cell-envelope disordering compound is myristyl alcohol.

13. A composition according to claim 8 wherein the level of any specific member of the $C_{16}$–$C_{20}$ straight chain, saturated normal fatty alcohols, and $C_4$–$C_{20}$ straight chain, saturated mono- or dicarboxylic acids is less than about 3.5% by weight.

14. A composition according to claim 13 wherein the level of any specific member of the $C_{16}$–$C_{20}$ straight chain, saturated normal fatty alcohols, and $C_4$–$C_{20}$ straight chain, saturated mono- or dicarboxylic acids is less than about 1% by weight.

15. A composition according to claim 8 which is substantially free from octanoic acid, decanoic acid, cetyl alcohol and stearyl alcohol.

16. A method of treating nonendocrine immunologic, rheumatic, hypersensitivity or inflammatory conditions in humans or lower animals comprising topically applying to a human or animal in need of such treatment a safe and effective amount of a composition according to claim 1.

17. A method according to claim 16 wherein the rheumatic or inflammatory condition is arthritis.

18. A method according to claim 16 wherein the rheumatic or inflammatory condition is rheumatic fever.

19. A method according to claim 16 wherein the hypersensitivity reaction is bronchial asthma.

20. A method according to claim 16 wherein the hypersensitivity reaction is anaphylaxsis.

21. A method according to claim 16 wherein the inflammatory condition is dermatitis.

22. A method according to claim 16 wherein the composition is applied at an application situs for systemic treatment.

23. A method according to claim 22 wherein the composition is applied from a sustained release device.

24. A method according to claim 21 wherein the composition is applied topically to the afflicted situs.

25. A method of treating nonendocrine immunologic, rheumatic, hypersensitivity or inflammatory conditions in humans or lower animals comprising topically applying a to human or animal in need of such treatment a safe and effective amount of a composition according to claim 8.

26. A method according to claim 25 wherein the rheumatic or inflammatory condition is arthritis.

27. A method according to claim 25 wherein the rheumatic or inflammatory condition is rheumatic fever.

28. A method according to claim 25 wherein the hypersensitivity reaction is bronchial asthma.

29. A method according to claim 25 wherein the hypersensitivity reaction is anaphylaxsis.

30. A method according to claim 25 wherein the inflammatory condition is dermatitis.

31. A method according to claim 25 wherein the composition is applied at an application situs for systemic treatment.

32. A method according to claim 31 wherein the composition is applied from a sustained release device.

33. A method according to claim 30 wherein the composition is applied topically to the afflicted situs.

34. A penetration-enhancing pharmaceutical composition for topical application, comprising:
  (a) a safe and effective amount of a pharmaceutically-active corticosteroid;
  (b) 0% to about 80% by weight of a solvent selected from the group consisting of water, ethanol or 2-propanol; and
  (c) about 10% to about 99.9% by weight of a penetration-enhancing carrier consisting essentially of:
    (i) 1,2-butanediol, and
    (ii) a cell-envelope disordering compound selected from the group consisting of methyl laurate, oleic acid, oleyl alcohol, monoolein, myristyl alcohol, or mixtures thereof;

wherein said 1,2-butanediol and said cell-envelope disordering compound are present in a ratio of diol:cell-envelope disordering compound of from about 1:1 to about 500:1 by weight; and wherein said penetration-enhancing composition is substantially free from any single member of the $C_{16}$–$C_{20}$ straight chain, saturated normal fatty alcohols, and $C_4$–$C_{20}$ straight chain, saturated mono- or dicarboxylic acids.

* * * * *